United States Patent [19]

Patil et al.

[11] Patent Number: 4,966,914
[45] Date of Patent: * Oct. 30, 1990

[54] OCULOSELECTIVE BETA-BLOCKERS AS ANTIGLAUCOMA AGENTS

[75] Inventors: Ghanshyam Patil, Vernon Hills, Ill.; William L. Matier, Hockessin, Del.; Khuong H. X. Mai, Chatworth, Calif.

[73] Assignee: E. I. Du Pont de Nemours and Company, Wilmington, Del.

[*] Notice: The portion of the term of this patent subsequent to Jan. 30, 2007 has been disclaimed.

[21] Appl. No.: 285,007

[22] Filed: Dec. 15, 1988

[51] Int. Cl.$^5$ .............................................. A61K 31/24
[52] U.S. Cl. .................. 514/461; 544/162; 546/237; 548/215; 548/237; 548/538; 549/372; 549/425; 549/487; 560/110; 514/237.8; 514/330; 514/374; 514/428; 514/451; 514/452; 514/487
[58] Field of Search ............... 549/487, 425, 372; 514/461, 237.8, 374, 451, 452, 330, 428, 487; 560/110; 544/162; 548/237, 215, 538; 546/237

[56] References Cited

U.S. PATENT DOCUMENTS

| | | | |
|---|---|---|---|
| 4,195,085 | 3/1980 | Stone. | |
| 4,402,974 | 9/1983 | Matier et al. | 560/110 |
| 4,405,642 | 9/1983 | Kam et al. | 560/110 |
| 4,579,867 | 4/1986 | Escobar et al. | 514/544 |
| 4,582,855 | 4/1986 | Kam et al. | 514/478 |
| 4,661,513 | 4/1987 | Bertholdet al. | 549/525 |
| 4,840,963 | 6/1989 | Shepard | 548/237 |
| 4,847,269 | 7/1989 | Clark et al. | 514/428 |
| 4,897,417 | 1/1990 | Patil et al. | 549/487 |

OTHER PUBLICATIONS

Liu et al., Invest. Ophthalmol. Vis. Sci, vol. 24, pp. 1276-1282 (1983).
Zimmerman et al, Survey Ophthalmol, vol. 23, pp. 347-362 (1979).
Boger, Drugs, vol. 18, pp. 25-32 (1979).

Primary Examiner—Donald G. Daus
Attorney, Agent, or Firm—Gildo E. Fato

[57] ABSTRACT

In accordance with the present invention, disclosed herein are compounds of the formula

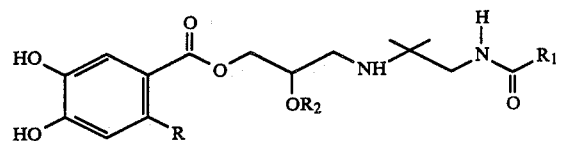

wherein R is hydrogen, straight or branched loweralkyl, cycloalkyl, amino, loweralkoxy or acylamino, and $R_1$ is straight or branched loweralkyl, amino, cyclohexyl phenyl or phenyl substituted with loweralkyl, loweralkoxy or halo, benzyl, morpholino, piperidino, tetrahydrofuranyl, dihydrofuranyl, furanyl, tetrahydropyranyl, dioxolanyl, 2,2-dimethyl dioxolanyl, dioxanyl, pyrrolidinyl, tetrahydrooxazolyl, and dihydrooxazolyl, $R_2$ is hydrogen or $-COR_3$ wherein $R_3$ is straight or branched loweralkyl, provided, however, when $R_1$ is loweralkyl or cyclohexyl, $R_2$ is not hydrogen, and pharmaceutically acceptable salts thereof. The compounds are useful in the treatment of glaucoma.

34 Claims, No Drawings

OCULOSELECTIVE BETA-BLOCKERS AS ANTIGLAUCOMA AGENTS

BACKGROUND OF THE INVENTION

Glaucoma is a condition of the eye characterized by increased intraocular pressure. Untreated, the condition can eventually lead to irreversible retinal damage and blindness. Conventional therapy for glaucoma has involved topical administration of pilocarpine and/or epinephrine, and more recently beta-blockers, such as Timolol, administered to the eye several times daily.

Various beta-blocking agents may also be used to lower intraocular pressure. Such use is described, for example, in reviews by W. P. Boger in *Drugs*, 18, 25-32 (1979) and by T. J. Zimmerman and W. P. Boger in *Survey Ophthalmol.* 23(b), 347 (1979). The use of beta-blockers for the treatment of glaucoma is also described in the patent literature. For example, U.S. Pat. No. 4,195,085 to Stone discloses a method for treatment of glaucoma by the ocular administration of a beta-blocking compound, timolol maleate. However, these methods also possess significant drawbacks, in that the absorption of the beta-blocking compound into the systemic circulation can cause undesirable life-threatening side effects. Such side effects result from prolonged beta-blocking action on the heart, bronchioles and blood vessels. Accordingly, there is a need for compounds and a method of treatment of glaucoma or for lowering intraocular pressure which is relatively free of unwanted systemic side effects.

Certain beta-blocking agents which contain enzymatically labile ester groups are known to exhibit short-acting beta-blocking effects in the systemic circulation. Such short-acting beta-blocking compounds (SAABs) have been suggested for treatment or prophylaxis of cardiac disorders as a means for reducing heart work or improving rhythmicity for a short duration. Such short-acting beta-blocking compounds avoid the sometimes counterproductive effects of conventional beta-blocking agents, whose effects are long-lived and, therefore, difficult to precisely control. Beta-blocking agents having such properties are described in U.S. Pat. Nos. 4,402,974, Sept. 6, 1983; 4,454,154, June 12, 1984; and 4,455,317, June 19, 1984.

SUMMARY OF THE INVENTION

In accordance with the present invention, disclosed herein are compounds of the formula

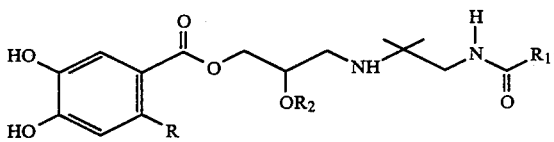

wherein R is hydrogen, straight or branched loweralkyl, cycloalkyl, amino, loweralkoxy or acylamino, and $R_1$ is straight or branched loweralkyl, amino, cyclohexyl, phenyl or phenyl substituted with loweralkyl, loweralkoxy or halo, benzyl, morpholino, piperidino, tetrahydrofuranyl, dihydrofuranyl, furanyl, tetrahydropyranyl, dioxolanyl, 2,2-dimethyl dioxolanyl, dioxanyl, pyrrolidinyl, tetrahydrooxazolyl, and dihydrooxazolyl, $R_2$ is hydrogen or $-COR_3$ wherein $R_3$ is straight or branched loweralkyl, provided, however, when $R_1$ is loweralkyl or cyclohexyl, $R_2$ is not hydrogen, and pharmaceutically acceptable salts thereof. The compounds are useful in the treatment of glaucoma.

DETAILED DESCRIPTION OF THE INVENTION

The compounds of the present invention are ester group containing beta-blockers that have a selective, localized, beta-blocking effect in the eye after topical administration. Such compounds are thought to be rapidly metabolized upon entering the systemic circulation and, therefore, will not be available to act on the receptor in the heart and the lungs. It has been discovered that these same compounds are relatively stable in ocular fluids, i.e., lacrimal fluids and aqueous humor, and ocular tissue such as iris-ciliary complex. Consequently, such compounds are useful for the treatment of glaucoma or for lowering intraocular pressure since they remain stable when topically applied to the eye but rapidly metabolize when subsequently absorbed into the systemic circulation. Thus, the method of the present invention provides a very useful therapeutic alternative for the treatment of glaucoma or for lowering intraocular pressure.

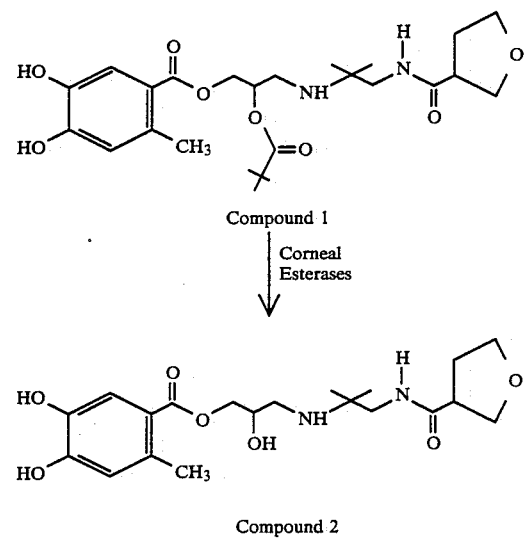

Compound 1

Corneal Esterases

Compound 2

Compound 1 is a prodrug of compound 2. Since compound 1 is considerably lipophilic, it is expected to penetrate the cornea much more rapidly and effectively.

The above-mentioned oculoselective beta-blocking compounds will effectively reduce intraocular pressure in the eyes of mammals when topically administered. Because of their short-lived duration of action in the systemic circulation, they will be unavailable to cause severe side effects. Consequently, the present invention resides in the treatment of glaucoma or lowering intraocular pressure with a beta-blocking compound which exhibits relatively long duration of action while in the ocular fluid, but which is subject to relatively rapid breakdown upon passage to the systemic circulation.

Compounds of the present invention are represented by the formula:

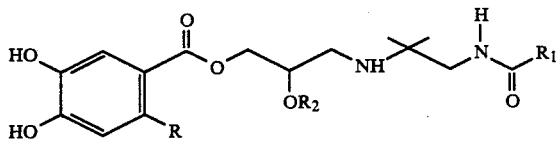

wherein R is hydrogen straight or branched loweralkyl, cycloalkyl, amino, loweralkoxy or acylamino, and $R_1$ is straight or branched loweralkyl, amino, cyclohexyl, phenyl or phenyl substituted with loweralkyl, loweralkoxy or halo, benzyl, morpholino, piperidino, tetrahydrofuranyl, dihydrofuranyl, furanyl, tetrahydropyranyl, dioxolanyl, 2,2-dimethyl dioxolanyl, dioxoanyl, pyrrolidinyl, tetrahydrooxazolyl, and dihydrooxazolyl, $R_2$ is hydrogen or —$COR_3$ wherein $R_3$ is straight or branched loweralkyl, and pharmaceutically acceptable salts thereof.

Illustrative preferred compounds in accordance with the present invention include, but are not limited to, those in which R is hydrogen or straight or branched loweralkyl, RI is straight or branched lower-alkyl, cyclohexyl, morpholino, tetrahydropyranyl or tetrahydrofuranyl, and $R_2$ is hydrogen.

The term "loweralkyl" as used herein refers to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "cycloalkyl" as used herein refers to cyclic saturated aliphatic radicals containing 3 to 12 carbon atoms in the ring, such as cyclopropyl, cyclobutyl, cyclopentyl, cyclohexyl, cyclododecyl, or adamantyl.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, and like salts. Also included are metallic salts such as the sodium or potassium salt of the acid.

The compounds of this invention are advantageously administered topically to the eye in the form of a solution, ointment, or solid insert such as is described in U.S. Pat. No. 4,195,085. Formulations may contain the active compound preferably, in the form of a soluble acid addition salt, in amounts ranging from about 0.01% to about 10% by weight, preferably, from about 0.5% to about 5% by weight. Unit dosages of the active compound can range from about 0.001 to about 5.0 mg, preferably from about 0.05 to about 2.0 mg. The dosage administered to a patient will depend upon the patient's needs and the particular compounds employed.

Carriers used in the preparations of the present invention are preferably nontoxic ophthalmologically acceptable pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. In addition, the pharmaceutical preparations may also contain additional components such as emulsifying, preserving, wetting and sterilizing agents. These include polyethylene glycols 200, 300, 400, and 600, carbowaxes 1,000, 1,500, 4,000, 6,000, and 10,000 bacteriocidal components such as quaternary ammonium compounds, phenylmercuric salts known to have cold sterilizing properties and which are noninjurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The method of treatment of this invention advantageously involves the topical administration of eye drops containing the active compound. Formulations for eye drops preferably include the active compound as a soluble acid addition salt in a properly buffered, sterile, aqueous isotonic solution.

The compounds of the present invention are ester group-containing beta-blockers that have a selective, localized, beta-blocking effect in the eye after topical administration. Such compounds are thought to be rapidly metabolized by plasma and/or liver esterases into inactive by-products, upon entering the systemic circulation. It has been discovered that these same compounds are relatively stable in ocular fluids, i.e., lacrimal fluids and aqueous humor. Consequently, such compounds are useful for the treatment of glaucoma or for lowering intraocular pressure since they remain stable when topically applied to the eye but rapidly metabolize when subsequently absorbed into the systemic circulation.

The compounds of the present invention and equivalents thereof possessing substantially similar pharmacological properties may be prepared according to the following reaction schemes, which represent specific embodiments of the invention.

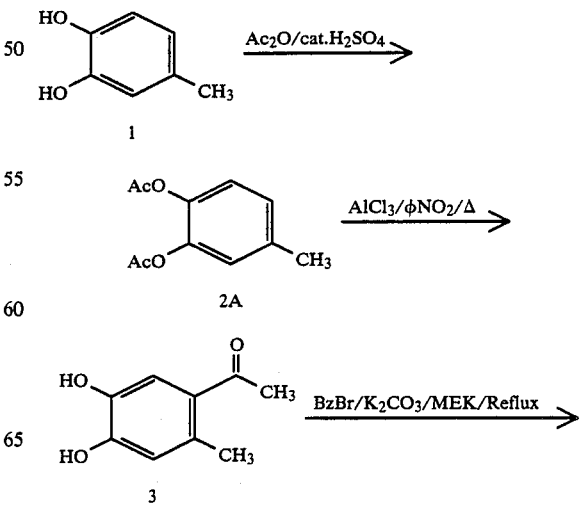

-continued
Synthesis of Compound 1 and 2
Scheme 1

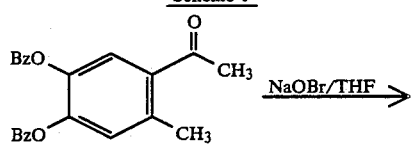

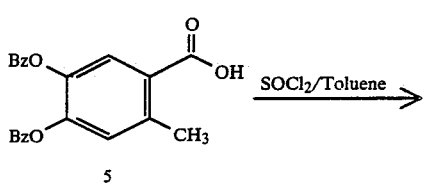

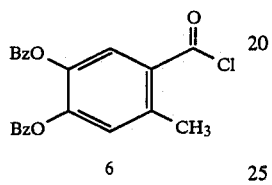

Bz = —CH₂C₆H₅

-continued
Synthesis of Compound 1 and 2
Scheme 2

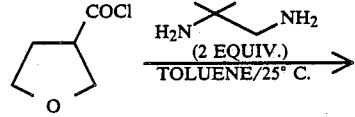

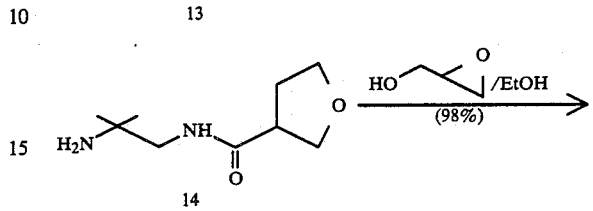

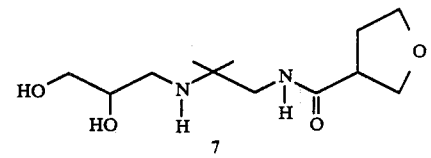

Synthesis of Compound 1 and 2
Scheme 3

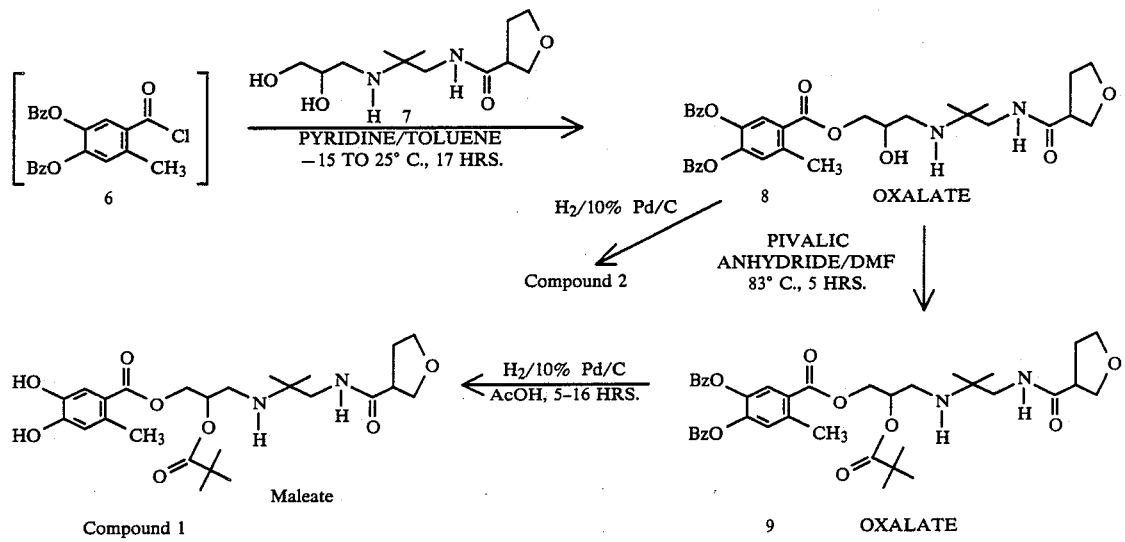

Synthesis of Compound 1 and 2
Scheme 2

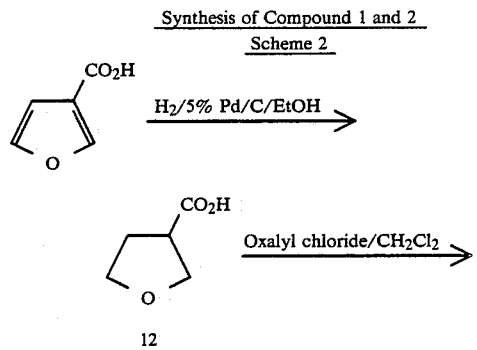

The following examples are intended to be illustrative of the present invention but should not be considered as limiting the scope thereof.

EXAMPLE 1

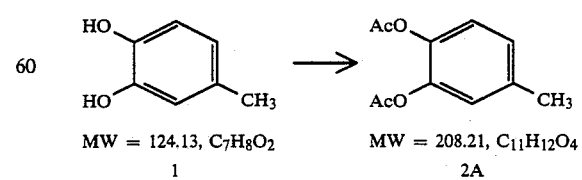

MW = 124.13, C₇H₈O₂   MW = 208.21, C₁₁H₁₂O₄
1                      2A

A solution of methylcatechol 1 (200 g, 1.61 moles) in acetic anhydride (415 g, 4.06 moles) was cooled in ice-bath and concentrated H₂SO₄ (2 drops) was added with stirring. A white precipitate gradually appeared and the temperature rose to 98° C. in 45 minutes. The reaction mixture was allowed to cool to 25° C., isopropyl ether (400 mL) was added, and the mixture was warmed (40° C.) to dissolve the precipitate. Water (400 mL) was added to the resulting solution and the organic layer was separated, washed with saturated sodium bicarbonate (300 mL), and dried (Na₂SO₄). Solvent removal in vacuo gave an oil which was dissolved into hexane (200 mL) and upon standing overnight in the cold afforded 315 g (94%) of crystalline 2A which was collected, washed with hexane, and air dried: m.p. 58°-61° C., TLC (EtOAc:Toluene, 1:3), Rf SM =0.6, Rf PROD =0.7.

EXAMPLE 2

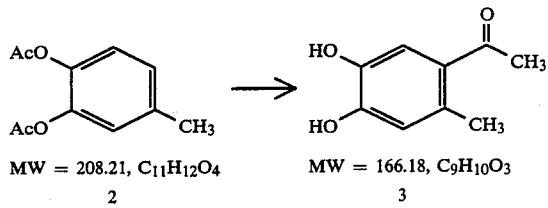

MW = 208.21, C₁₁H₁₂O₄
2

MW = 166.18, C₉H₁₀O₃
3

The diacetoxy catechol 2 (300 g, 1.44 moles) was dissolved in nitrobenzene (700 g) with stirring. Aluminum chloride (500 g, 3.75 moles) was added to this solution in 5 portions with the temperature of the solution rising to 40° C. during the addition. This mixture was heated at 85° C. for 90 minutes, and then cooled to room temperature. Ice (400 g) was carefully added in small portions (caution: vigorous reaction!) followed by concentrated HCl solution (400 g) (exothermic!) and ice (400 g). The mixture which now contains solid precipitate was stirred for 16 hours. The solid was collected and washed with hexane (400 mL) to give 380 g of wet product which upon drying in a vacuum oven afforded 209 g (87%) of 3: m.p. 168°-169° C.; TLC (EtOAc:Toluene, 1:3) Rf SM=0.7, Rf PROD=0.5.

EXAMPLE 3

MW = 166.18, C₉H₁₀O₃
3

MW = 346.43, C₂₃H₂₂O₃
4

A mixture of catechol 3 (600 g, 3.61 moles), benzylbromide (1.29 L) and potassium carbonate (1.5 kg) in MEK (3 L) was heated under reflux with stirring (mechanical) for 18 hours. The warm solution was filtered and the collected residue was washed with MEK (5×300 mL). The combined filtrates were evaporated in vacuo to give an oil (860 g) which was crystallized from isopropylether/hexane then recrystallized from isopropyl ether to give 800 g (62%) of 4 as a light yellow solid: m.p. 71°-72° C.; TLC (EtOAc:Hexane, 1:3) Rf SM=0.2, RF PROD=0.6.

EXAMPLE 4

MW = 346.43, C₂₃H₂₂O₃
4

MW = 348.40, C₂₂H₂₀O₄
5

To a mixture of sodium hydroxide (69.3 g of 50% solution, 0.866 moles) and ice (200 g) was added bromine (48 g, 0.3 mole) in one portion, with vigorous stirring. This resulting solution was added to an ice-cooled solution of acetophenone 4 (34.65 g, 0.1 mole) in dioxane (230 mL) in one portion. After 1 hour, THF (100 mL) and water (50 mL) were added and stirring was continued for another 16 hours. The organic layer was then separated and the THF was removed in vacuo affording an aqueous (dioxane) residual solution. This solution was combined with the aqueous layer, cooled in an ice-bath and acidified with concentrated HCl solution (90 mL). After stirring for 1 hour in the cold, the mixture was allowed to stand for 16 hours at room temperature. The crystallized solid was collected and washed with water and hexane. The wet cake was dissolved into chloroform, dried (MgSO₄), and filtered. Solvent removal in vacuo gave a solid residue which was dried in vacuo to give 35 g (quantitative) of dibenzyloxy derivative 5 m.p. 163°-165° C.; TLC (EtOAc:Toluene, 15:85) Rf SM=0.8; Rf PROD =0.95.

EXAMPLE 5

MW = 348.40, C₂₂H₂₀O₄
5

MW = 366.85, C₂₂H₁₉O₃Cl
6

7
MW = 261.35, C₁₂H₂₄N₂O₄

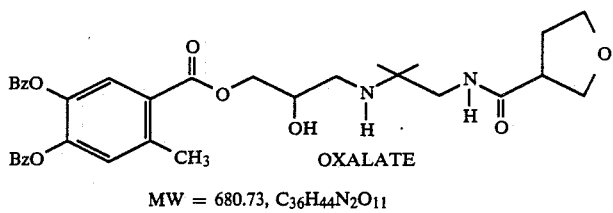

MW = 680.73, C$_{36}$H$_{44}$N$_2$O$_{11}$

8

A mixture of acid 5 (5.92 g, 0.17 moles), toluene (20 mL), and thionyl chloride (12.3 mL) was heated under reflux for 3 hours and the volatiles were evaporated. The residue was then coevaporated with toluene (3 times). The resulting oil was redissolved into toluene (5 mL) and added to an ice-cooled solution of the diol 7 (14.5 g, 0.16 moles) in 15 mL toluene and 15 mL pyridine. The ice-bath was removed and the reaction mixture was stirred at room temperature for 2 hours. The solvent was then removed in vacuo and the residue coevaporated with toluene (5 times). The residue was partitioned between ethyl/acetate and water and was made basic (pH 11) with potassium carbonate. The organic layer was separated, evaporated and the residue coevaporated with toluene (3 times). The resulting thick oil was redissolved in ethyl/acetate (55 mL) and the solution was acidified with oxalic acid predissolved in ethyl/acetate. The crystalline material thus obtained was collected, washed with a little ethlyl acetate followed by ether and air dried to give 4.43 g of product 8 in the first crop and 1.08 g in the second crop. (51.1%): m.p. (128° C., shrinks) 135°-36° C., TLC (EtOAc;3:1); Rf diol SM=0.1; Rf PROD =0.35.

EXAMPLE 6 mmole), and dimethylformamide (400 mL) was heated in an oil bath at 83° C. with mechanical stirring for five hours. The resulting dark solution was evaporated under vacuum and the residue taken up in ethyl ether (2000 mL). The solution, which contained some undissolved dark oil, was washed with 1 M potassium carbonate solution (3×800 mL), water (800 mL), and saturated sodium chloride solution (800 mL). After drying over magnesium sulfate, the dark solution was evaporated under vacuum to yield 160 g of dark red oil. This oil was taken up in ethyl acetate (700 mL), and oxalic acid (26.84 g) was added. The mixture was heated on a steam bath until a solution was formed, seeded, and placed in a freezer (−20° C.) for 16 hours. Ethyl ether (200 mL) was added, and the gelatinous precipitate was thoroughly broken up, collected, and pressed to remove as much solvent as possible. The product was then washed with 2:1 ethyl acetate: ethyl ether (600 mL), 1:1 ethyl acetate: ethyl ether (300 mL), and ethyl ether (2×600 mL) and pressed after each washing to remove as much solvent as possible. The resulting light tan product 9 was air dried for 15 minutes, and then immediately placed under vacuum at 56° C. to dry for 4 hours. Yield: 105.49 g (46.9%) tan solid.

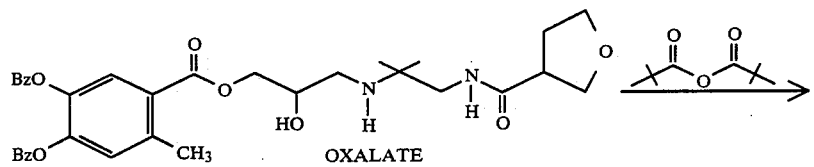

8

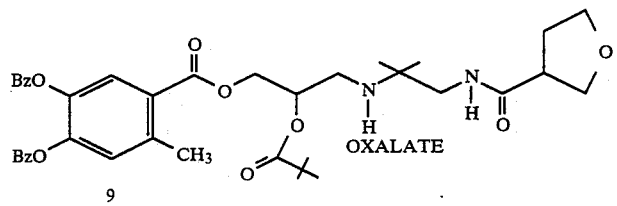

9

A mixture of the beta-hydroxy ester 8 1200.0 g; 294 mmole), trimethylacetic anhydride (120 mL; 591

EXAMPLE 7

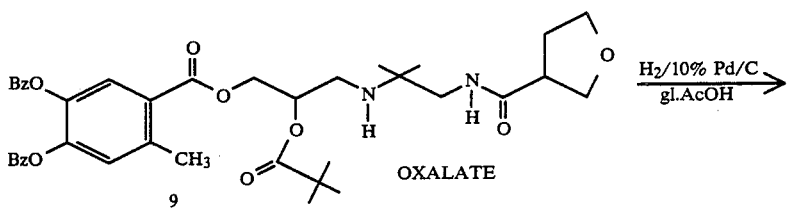

MW = 765.89, C₄₁H₅₃N₂O₁₂

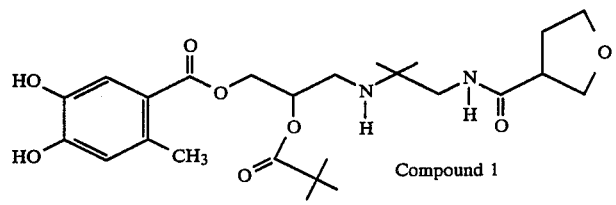

MW = 610.67, C₂₉H₄₂N₂O₁₂

To diester 9 (10 g, 13.1 mmoles) in acetic acid (100 mL) was added 10% palladium on charcoal (1.0 g) and the mixture was hydrogenated in a Parr apparatus at 37 psi for 5.5 hours. The solution was filtered through celite, and the solvent removed in vacuo and the residue was coevaporated once with toluene. To this residue was added ethyl acetate (100 mL) and saturated sodium bicarbonate (100 mL) and the mixture was stirred. After most of the residue was dissolved, the aqueous layer was separated and extracted twice with ethyl acetate. The organic extracts were combined, washed with saturated sodium bicarbonate solution and brine, dried over MgSO₄ and filtered. The solution was stirred for 30 minutes with maleic acid (1.67 g), and the resulting precipitate was collected, washed with ethyl acetate, acetone and ether, respectively (Compound 1). The crystalline solid was air dried affording 5.8 g (72.5%) of 10 m.p. 179°–181° C.

EXAMPLE 8

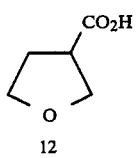

12

The acid 12 was synthesized by the procedure described in JACS 80, 3905 (1958).

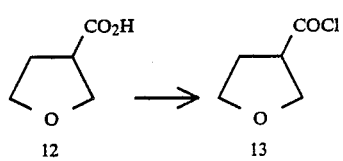

To a solution of acid 12 (29 g, 250 mmoles) in methylene chloride (100 mL), cooled to −5° C. and to this was added oxalyl chloride (39 g, 300 mmoles) under nitrogen over 30 minutes. The cooling bath was removed and the reaction was stirred at room temperature for 1½ hours and then heated under reflux for 3 hours. After solvent removal, the residue was co- evaporated with toluene, and then distilled at 77°–84° C. to give 25 g (74%) of 13.

EXAMPLE 9

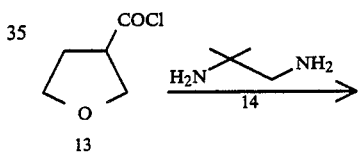

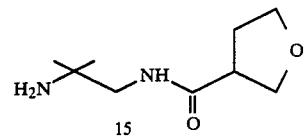

To an ice-cooled solution of diamine 14 (7.9 g, 89 mmoles) in toluene (50 mL) was added the acid chloride 13 (6.1 g, 89 mmole) and the mixture was stirred at room temperature for 16 hours. The solution was filtered and the filtrate was evaporated to dryness in vacuo. The residue was coevaporated in vacuo with toluene and acetonitrile, respectively, to give 7.82 g of oil. The oil was redissolved in toluene (50 mL) and the solution was washed with saturated sodium bicarbonate solution, followed by brine, dried (MgSO₄), filtered and evaporated to dryness under high vacuum to give 7.32 g of oil which was used as is in the next experiment.

EXAMPLE 10

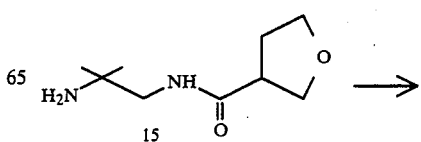

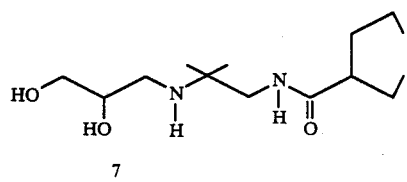

The solution of the aminoamide 15 (98.3 g, 0.55 moles) and glycidol (32.6 g, 0.44 moles, freshly distilled) in ethanol (600 mL) was heated under reflux for 1½ hours and then stirred for 16 hours at room temperature. The reaction mixture was evaporated to dryness in vacuo and the residue was coevaporated in vacuo with toluene (3 times) and acetonitrile (once), respectively, to yield 114.5 g (0.44 moles, 80%) of 7 which was used as is in the next step (see Example 5).

Stereoisomers

Compounds in accordance with the present invention exist as stereoisomers, as represented by the following formulas, due to the presence of asymmetric carbon atoms. The invention includes the stereoisomeric forms, as well as the racemic mixtures.

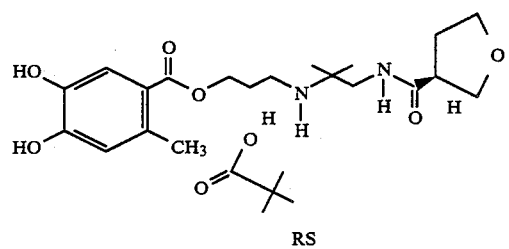

(1)

RS

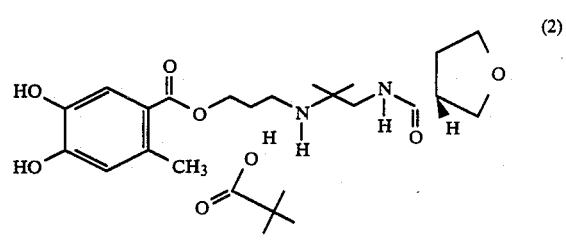

(2) RR

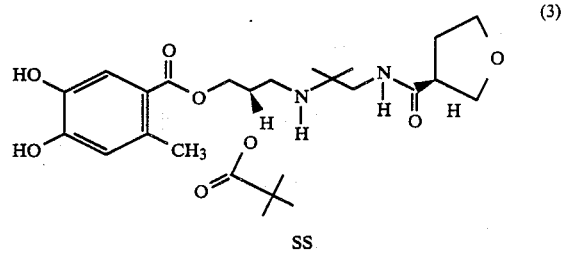

(3) SS

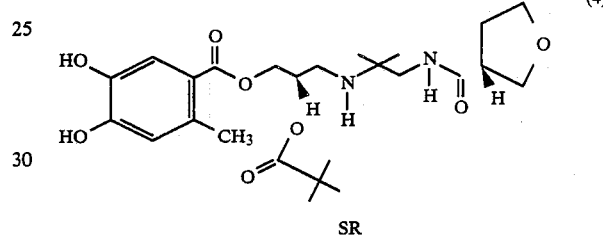

(4) SR

The chiral compounds can be prepared by an asymmetric synthesis such as represented by the following reaction scheme.

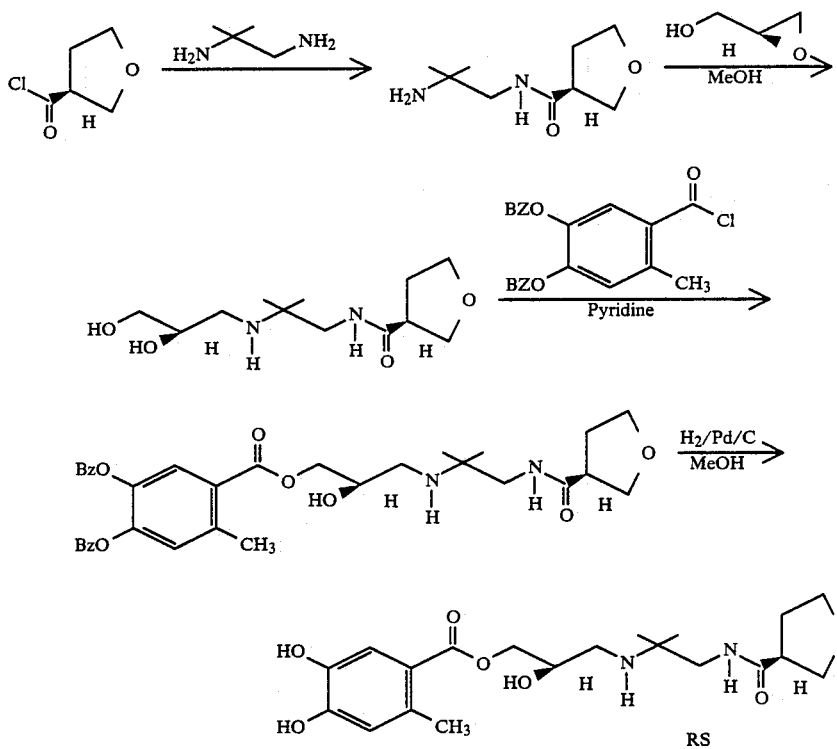

Compound 1

Ocular Bioavailability in Rabbits

The ocular bioavailability of Timolol and compound 1 (monopivaloyl ester prodrug of compound 2) was evaluated in New Zealand White Rabbits. Fifty μL of a solution of 0.25% Timolol or 0.5% compound 1 (both in the same vehicle) were administered onto the cornea of both eyes of 48 rabbits (24 rabbits/compound). At 5, 15, 30, 60, 120, 180, 240, and 360 minutes after dosing, 3 rabbits (6 eyes)/compound were killed. The cornea, aqueous humor (AH), iris-ciliary body complex (I-CBC) were quickly removed from the eyes, weighed and processed to determine tissue levels of Timolol or compound 1 and compound 2.

The results indicate that Timolol was rapidly absorbed across the cornea into the AH and I-CBC. Peak cornea levels (770 ng/50 mg) occurred at 5 minutes post dosing. Timolol levels peaked at 30 minutes in both AH (131 ng/100 μL) and I-CBC (58 ng/50 mg). The area under the concentration time curve (AUC$_{0-240'}$) for cornea, AH and I-CBC averaged 68,293 ng/50 mg/min, 9,022 ng/100 μL/min and 533 ng/50 mg/min, respectively.

Compound 1 was also rapidly absorbed across the cornea and metabolized to compound 2 the active compound. Peak levels of compound 1 in cornea and AH occurred at 5 and 30 minutes, respectively, compound 1 was not detectable in I-CBC. Consistent with the rapid metabolism of compound 1 to compound 2, very high levels of compound 2 (452 ng/50 mg) were present in cornea at 5 minutes after administration of compound 1. Cornea levels of compound 2 peaked at 30 minutes (1,497 ng/50 mg). AH levels of compound 2 rapidly increased from 30 ng/100 μL at 15 minutes to a peak concentration of 140 ng/100 μL at 120 minutes. I-CBC levels of compound 2 remained fairly constant between 30 to 120 minutes post dosing averaging 20 to 30 ng/50 mg during that time period. The AUC0-240' of compound 2 in cornea, AH and I-CBC averaged 95,789 ng/50 mg/min, 27,377 ng/100 μL/min and 2,981 ng/50 mg/min, respectively.

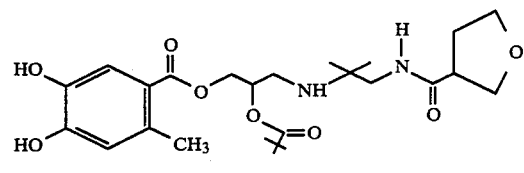

1

2

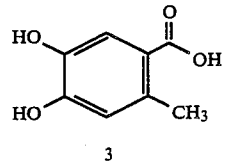

3

Based on the ocular bioavailability results, the AUC of compound 1 in AH after 0.5% compound 1 is 3× greater than the AUC of Timolol in AH after 0.25% Timolol.

It is concluded that compound 1 effectively delivers compound 2 to the internal structures of the eye and that compound 2 is stable in rabbit ocular tissues.

Effect of Compound 1 on Systemic Beta-Blockade Upon Topical Administration

Mongrel dogs were anesthetized and control readings were made at −45 and −30 minutes. Following the −30 minute reading, an infusion of isoproterenol (0.5 μg/kg/min) was begun and maintained during the course of the experiment. Two readings of pretreatment isoproterenol responses were made at 15 minutes and at zero minutes.

At zero minutes, a 50 μL sample of test compound was administered topically. This dose was repeated at 50, 60 and 90 minutes and the animal was monitored for heart rate for 180 minutes following the first application. Heart rate was obtained directly from the strip chart recording.

Compound 1 upon either single or repeated (Table 1) topical applications (50 μL, 0.25% solution) had no effect on either the heart rate or the diastolic blood pressure responses to isoproterenol. Compound 1 (50 μL at 0.5 or 1.0% solution) demonstrated no significant systemic beta-blockade of isoproterenol-induced increase in heart rate (199–193 bbm) and was without any significant effect on the diastolic blood pressure response to isoproterenol (58–63 mmHg). By contrast, Timolol (50 μL, 0.25% solution) upon single topical application demonstrated a significant inhibitory effect on the heart rate response to isoproterenol (197–155 bbm) and a long lasting antagonism of the diastolic blood pressure response to isoproterenol (72–107 mmHg). Furthermore, four topical applications of Timolol (50 μL, 0.25% solution) at 60 minute intervals produced a prolonged systemic beta-blockade.

It is concluded that compound 1 has systemic beta-blocking activity as compared to Timolol. Further, unlike Timolol, the peripheral effects of high concentration of compound 1 are selective for beta-1 (heart rate) responses.

The in vitro potency (pA2), in vivo potency and duration of action (DOA) of the compounds of the present invention are recorded in Tables 2 to 4. These pharmacological activities were determined using the methods described in U.S. patent 4,582,855 issued Apr. 15, 1986, and demonstrate the short-acting beta-blocking effects of the compounds of this invention.

TABLE 1

The Effects of Topically Administered Compound 1 or Timolol on Isoproterenolol-Induced Changes in Heart Rate or Diastolic Blood Pressure in Anesthetized Dogs

| Treatment Group | Parameter | Baseline ISO Only −30 | 0 Dose | 15 | 30 | 45 | 60 Dose | 75 | 90 | 105 | 120 Dose | 135 | 150 | 165 | 180 |
|---|---|---|---|---|---|---|---|---|---|---|---|---|---|---|---|
| Compound 1 0.5% (n = 4) | HR (bpm) | 143 ±8 | 199 ±11 | 195 ±12+ | 192 ±12 | 188 ±14 | 189 ±13 | 189 ±13 | 189 ±14 | 190 ±13 | 192 ±14 | 192 ±14 | 192 ±14 | 192 ±14 | 193 ±14 |
| | DBP (mmHg) | 87 ±8 | 58 ±5 | 56 ±5 | 55 ±5 | 54 ±5 | 55 ±4 | 55 ±4 | 56 ±4 | 57 ±3 | 59 ±4 | 61 ±4 | 60 ±4 | 60 ±3 | 63 ±4 |
| Timolol 0.5% (n = 3) | HR (bpm) | 144 ±6 | 197 ±18 | 175 ±13 | 158 ±6 | 155 ±6 | 157 ±8 | 157 ±8 | 152 ±9 | 153 ±9 | 157 ±11 | 154 ±10 | 153 ±10 | 153 ±11 | 159 ±11 |
| | DBP (mmHg) | 173 ±2 | 72 ±8 | 93 ±4 | 94 ±5 | 96 ±4 | 99 ±4 | 102 ±3 | 103 ±4 | 104 ±4 | 105 ±5 | 107 ±4 | 107 ±2 | 105 ±3 | 107 ±4 |
| Vehicle 0.5% (n = 4) | HR (Bpm) | 151 ±11 | 199 ±16 | 197 ±14 | 196 ±13 | 196 ±13 | 196 ±13 | 199 ±14 | 200 ±15 | 202 ±15 | 203 ±15 | 204 ±15 | 206 ±14 | 208 ±14 | 208 ±16 |
| | DBP (mmHg) | 110 ±7 | 76 ±6 | 76 ±7 | 74 ±7 | 74 ±8 | 73 ±8 | 76 ±7 | 75 ±8 | 76 ±8 | 76 ±9 | 78 ±8 | 77 ±8 | 77 ±9 | 78 ±9 |

Summary

| | BP (mmHg) | | Change | HR (bpm) | | Change |
|---|---|---|---|---|---|---|
| Compound 1 | 58–63 | = | down 5 | 199–193 | = | down 6 |
| Timolol | 71–107 | = | down 35 | 197–159 | = | down 38 |
| Vehicle | 76–78 | = | down 2 | 199–208 | = | up 9 |

HR = Heart Rate
bpm = beats per minute
DBP = Diastolic Blood Pressure
mmHg = millimeters of mercury

TABLE 2

Analogs of Compound 2

| $R_1$ | In-vitro potency $pA_2$ | In-vivo potency mcg/kg/min | DOA min. |
|---|---|---|---|
| isopropyl | 8.2 | 0.75 | 42 |
| cyclohexyl | 8.4 | 2.0 | 31/>60 |
| morpholino (–N<O) | 8.7 | 0.05 | 60 |
| tetrahydropyranyl | 8.3 | 0.28 | 26 |
| tetrahydrofuranyl | 8.8 | 0.12 | 49 |

TABLE 3

| R | $R_1$ | m.p. °C. | $pA_2$ ATRIA |
|---|---|---|---|
| H | tetrahydrofuranyl | 140–42 | 8.9 |
| Me | tetrahydrofuranyl | 130–40 | 8.8 |
| $NH_2$ | isopropyl | 115–19 | 7.1 |
| OMe | isopropyl | 193–95 | 7.9 |
| OMe | cyclohexyl | 102–10 | 7.6 |
| OEt | isopropyl | 163–65 | 7.7 |
| Me | —$CH_3$ | 166–69 | 7.6 |
| Me | ethyl | 145–50 | 8.0 |
| Me | propyl | 125–28 | 8.2 |

TABLE 3-continued

| R | R₁ | m.p. °C. | pA₂ ATRIA |
|---|---|---|---|
| Me |  | 145–50 | 8.2 |
| Me | 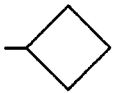 | 174–75 | 7.7 |
| Me | 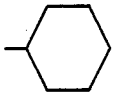 | 154–57 | 8.3 |
| Me | 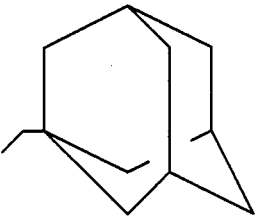 | 156–61 | 8.4 |
| Me | 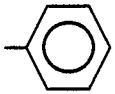 | 107–09 | 6.1 |
| Me | 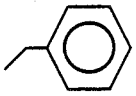 | 183–85 | 7.7 |
| Me | 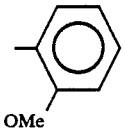 | 100–05 | 7.0 |
| Me | 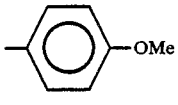 OMe | 160–63 | 6.4 |
| Me | 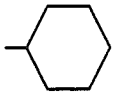 —OMe | 161–63 | 7.5 |
| H | 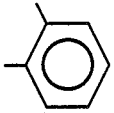 | 153–55 | 8.2 |
| Me |  F | 75–78 | 7.0 |
| Me |  | 166–69 | 7.6 |
| Me | —NH₂ | 60–70 | 8.9 |
| Me | 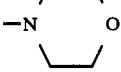 | 160–61 | 8.7 |
| Me | 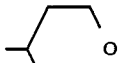 | 102–04 | 8.3 |

TABLE 4
Some ortho substituted analogs

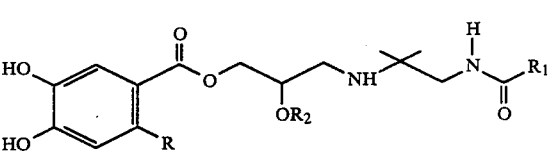

| R | In-vitro potency pA₂ | In-vivo potency mcg/kg/min | DOA min. |
|---|---|---|---|
| Me | 8.2 | 0.75 | 42 |
| OMe | 7.9 | 0.75 | 30 |
| OEt | 7.7 | 2.00 | 22 |
| NH₂ | 7.1 | — | — |

What is claimed is:

1. A compound of the formula

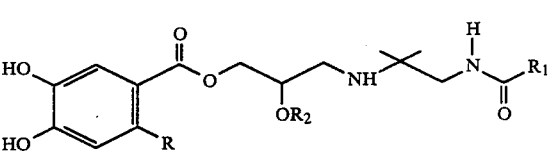

wherein R is hydrogen, straight or branched loweralkyl, cycloalkyl, amino, loweralkoxy or alkanoyl amino, and $R_1$ is straight or branched loweralkyl, amino, cyclohexyl, phenyl or phenyl substituted with loweralkyl, loweralkoxy or halo, benzyl, tetrahydrofuranyl, dihydrofuranyl, furanyl, $R_2$ is hydrogen or —COR₃ wherein $R_3$ is straight or branched loweralkyl, provided, however, when $R_1$ is loweralkyl, phenyl or cyclohexyl, $R_2$ is not hydrogen, or a pharmaceutically acceptable salt thereof.

2. A compound of claim 1 wherein R is hydrogen or loweralkyl, $R_1$ is loweralkyl, cycloalkyl, or tetrahydrofuranyl, and $R_2$ is hydrogen, —COR₃ or loweralkyl.

3. A compound of claim 2 wherein R is methyl, $R_1$ is propyl, cyclohexyl, or tetrahydrofuranyl, and $R_2$ is hydrogen or —COR₃.

4. A compound of the formula

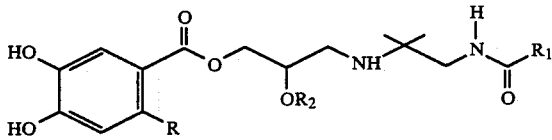

wherein R is hydrogen, loweralkyl, loweralkoxy or amino, $R_1$ is loweralkyl, cycloalkyl, benzyl, phenyl, phenyl substituted with methoxy or fluoro, furanyl, or tetrahydrofuranyl, and $R_2$ is hydrogen or —$COR_3$, wherein $R_3$ is straight or branched loweralkyl provided, however, when $R_1$ is loweralkyl, cycloalkyl or phenyl, $R_2$ is not hydrogen.

5. A compound of the formula

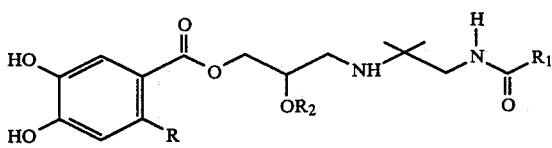

wherein R is loweralkyl, $R_1$ is loweralkyl or tetrahydrofuranyl, and $R_2$ is hydrogen, loweralkyl or —$COR_3$, wherein $R_3$ is straight or branched loweralkyl.

6. The compound of claim 5 wherein R is methyl, $R_1$ is tetrahydrofuranyl, and $R_2$ is hydrogen.

7. A method of treating glaucoma or of lowering intraocular pressure in a patient comprising administering to the eye of a patient in need of such treatment a therapeutically effective amount of a compound of the formula

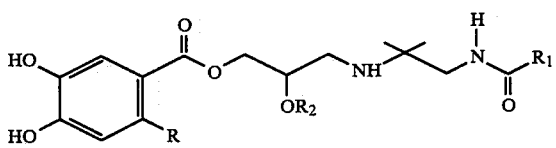

wherein R is hydrogen, straight or branched loweralkyl, cycloalkyl, amino, loweralkoxy or alkanoyl amino, and $R_1$ is straight or branched loweralkyl, amino, cyclohexyl, phenyl or phenyl substituted with loweralkyl, loweralkoxy or halo, benzyl, tetrahydrofuranyl, dihydrofuranyl, furanyl, $R_2$ is hydrogen or —$COR_3$ wherein $R_3$ is straight or branched loweralkyl, provided, however, when $R_1$ is loweralkyl, phenyl or cyclohexyl, $R_2$ is not hydrogen, or a pharmaceutically acceptable salt thereof.

8. The method of claim 7 wherein R is hydrogen or loweralkyl, $R_1$ is loweralkyl, cycloalkyl, or tetrahydrofuranyl, and $R_2$ is hydrogen, —$COR_3$ or loweralkyl.

9. The method of claim 8 wherein R is methyl, $R_1$ is propyl, cyclohexyl, or tetrahydrofuranyl, and $R_2$ is hydrogen or —$COR_3$.

10. The method of claim 7 wherein R is hydrogen, loweralkyl, loweralkoxy or amino, $R_1$ is loweralkyl, cycloalkyl, benzyl, phenyl, phenyl substituted with methoxy or fluoro, furanyl, or tetrahydrofuranyl and $R_2$ is hydrogen or —$COR_3$.

11. The method of claim 10 wherein R is loweralkyl, $R_1$ is loweralkyl or tetrahydrofuranyl, and $R_2$ is hydrogen, —$COR_3$ or loweralkyl.

12. The method of claim 11 wherein R is methyl, $R_1$ is tetrahydrofuranyl, and $R_2$ is hydrogen.

13. The method of claim 7 wherein the compound is administered as a solution of about 0.2% to about 5% by weight of the compound in an ophthalmologically acceptable carrier.

14. The method of claim 7 wherein the compound is contained in a sterile, aqueous, buffered, isotomic solution.

15. A pharmaceutical composition useful for the treatment of glaucoma or for lowering intraocular pressure, which composition comprises an intraocular lowering effective amount of a compound of the formula

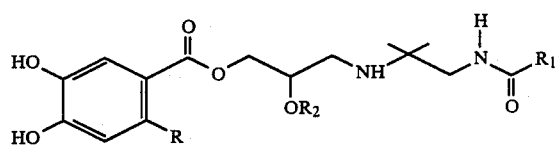

wherein R is hydrogen, straight or branched loweralkyl, cycloalkyl, amino, loweralkoxy or alkanoylamino, and $R_1$ is straight or branched loweralkyl, amino, cyclohexyl, phenyl or phenyl substituted with loweralkyl, loweralkoxy or halo, benzyl, tetrahydrofuranyl, dihydrofuranyl, furanyl, $R_2$ is hydrogen or —$COR_3$ wherein $R_3$ is straight or branched loweralkyl, provided, however, when $R_1$ is loweralkyl, phenyl or cyclohexyl, $R_2$ is not hydrogen, or a pharmaceutically acceptable salt thereof in admixture with an opthalmologically acceptable carrier or diluent.

16. The composition of claim 15 wherein R is hydrogen or loweralkyl, $R_1$ is loweralkyl, cycloalkyl, or tetrahydrofuranyl, and $R_2$ is hydrogen or —$COR_3$.

17. The composition of claim 16 wherein R is methyl, $R_1$ is propyl, cyclohexyl, or tetrahydrofuranyl, and $R_2$ is hydrogen or $COR_3$.

18. The composition of claim 15 wherein R is hydrogen, loweralkyl, loweralkoxy or amino, $R_1$ is loweralkyl, cycloalkyl, benzyl, phenyl, phenyl substituted with methoxy or fluoro, furanyl, morpholino or tetrahydropyranyl, and $R_2$ is hydrogen or —$COR_3$.

19. A pharmaceutical composition useful for the treatment of glaucoma or for lowering intraocular pressure, which composition comprises an intraocular lowering effective amount of a compound of the formula

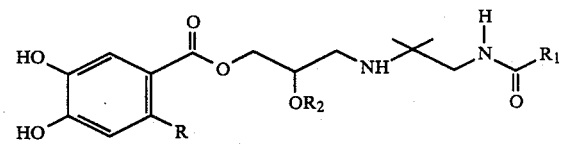

wherein R is loweralkyl, $R_1$ is loweralkyl or tetrahydrofuranyl, and $R_2$ is —$COR_3$ wherein $R_3$ is straight or branched loweralkyl or a pharmaceutically acceptable salt thereof in admixture with an opthalmologically acceptable carrier or diluent.

20. The composition of claim 17 wherein R is methyl, $R_1$ is tetrahydrofuranyl, and $R_2$ is hydrogen.

21. The stereoisomers of the compound of claim 12.

22. The compound of claim 5 wherein R is methyl, $R_1$ is tetrahydrofuranyl, and $R_2$ is —$COR_3$ wherein $R_3$ is straight or branched loweralkyl.

23. The compound of claim 22 wherein $R_3$ is butyl.

24. The compound of claim 23 wherein $R_3$ is t-butyl.

25. The method of claim 11 wherein R is methyl, $R_1$ is tetrahydrofuranyl, and $R_2$ is —$COR_3$ wherein $R_3$ is straight or branched alkyl.

26. The method of claim 25 wherein $R_3$ is butyl.

27. The method of claim 26 wherein $R_3$ is t-butyl.

28. The composition of claim 19 wherein R is methyl, $R_1$ is tetrahydrofuranyl, and $R_2$ is —$COR_3$ wherein $R_3$ is straight or branched alkyl.

29. The composition of claim 28 wherein R is butyl.

30. The composition of claim 29 wherein R is t-butyl.

31. A compound of the formula

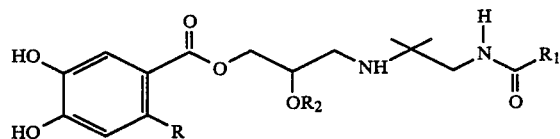

wherein R is hydrogen, straight or branched loweralkyl, cycloalkyl, amino, loweralkoxy or alkanoylamino, and $R_1$ is straight or branched loweralkyl, amino, cyclohexyl, phenyl or phenyl substituted with loweralkyl, loweralkoxy or halo, benzyl, tetrahydrofuranyl, dihydrofuranyl, furanyl, $R_2$ is —$COR_3$ wherein $R_3$ is straight or branched loweralkyl, or a pharmaceutically acceptable salt thereof.

32. A compound of claim 1 wherein R is loweralkyl, $R_1$ is loweralkyl, cycloalkyl, or tetrahydrofuranyl, and $R_2$ is —$COR_3$ is loweralkyl.

33. A compound of claim 2 wherein R is methyl, $R_1$ is propyl, cyclohexyl, tetrahydrooxazolyl, tetrahydropyranyl or tetrahydrofuranyl, and $R_2$ is hydrogen or —$COR_3$.

34. A compound of the formula

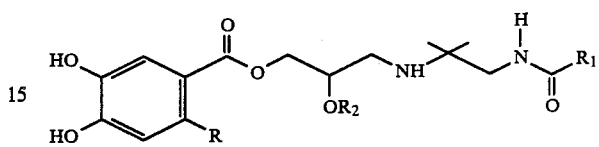

wherein R is loweralkyl, loweralkoxy or amino, $R_1$ is loweralkyl, cycloalkyl, benzyl, phenyl, phenyl substituted with methoxy or fluoro, furanyl, morpholino, or tetrahydropyranyl or tetrahydrofuranyl, and $R_2$ is —$COR_3$ wherein $R_3$ is straight or branched loweralkyl.

* * * * *